(12) United States Patent
Van Acker

(10) Patent No.: US 8,133,193 B2
(45) Date of Patent: Mar. 13, 2012

(54) METHOD FOR TREATMENT OF SKIN DISEASES AND THE LIKE

(76) Inventor: Ted Gerard Van Acker, Marion, IL (US)

( * ) Notice: Subject to any disclaimer, the term of this patent is extended or adjusted under 35 U.S.C. 154(b) by 246 days.

(21) Appl. No.: 12/506,763

(22) Filed: Jul. 21, 2009

(65) Prior Publication Data

US 2009/0281472 A1    Nov. 12, 2009

Related U.S. Application Data

(62) Division of application No. 11/080,707, filed on Mar. 15, 2005, now Pat. No. 7,582,067.

(51) Int. Cl.
*A61M 35/00* (2006.01)
(52) U.S. Cl. ............................. 604/1; 604/309
(58) Field of Classification Search ............... 604/1–3, 604/309
See application file for complete search history.

(56) References Cited

U.S. PATENT DOCUMENTS

| | | | | |
|---|---|---|---|---|
| 1,652,108 A * | 12/1927 | Forbis | ................. | 604/1 |
| 3,203,418 A * | 8/1965 | Johnston | ................. | 604/1 |
| 3,327,706 A * | 6/1967 | Watson, Sr. | ................. | 604/309 |
| 3,343,540 A * | 9/1967 | Siegel | ................. | 604/1 |
| 3,759,375 A * | 9/1973 | Nappi | ................. | 206/362 |
| 3,871,375 A * | 3/1975 | Bennett | ................. | 604/1 |
| 3,948,265 A * | 4/1976 | Al Ani | ................. | 604/309 |
| 3,976,195 A * | 8/1976 | Cohen | ................. | 206/362 |
| 4,259,955 A * | 4/1981 | Ritter | ................. | 604/1 |
| 4,473,156 A * | 9/1984 | Martin | ................. | 206/534 |
| 4,740,194 A * | 4/1988 | Barabino et al. | ................. | 604/3 |
| 4,795,421 A * | 1/1989 | Blasius et al. | ................. | 604/1 |
| 4,820,259 A * | 4/1989 | Stevens | ................. | 604/2 |
| 4,883,454 A * | 11/1989 | Hamburg | ................. | 604/1 |
| 4,887,994 A * | 12/1989 | Bedford | ................. | 604/1 |
| 5,016,659 A * | 5/1991 | Mas | ................. | 132/321 |
| 5,029,726 A * | 7/1991 | Pendill | ................. | 221/69 |
| 5,112,297 A * | 5/1992 | Stalcup et al. | ................. | 604/1 |
| 5,242,433 A * | 9/1993 | Smith et al. | ................. | 604/289 |
| 5,676,643 A * | 10/1997 | Cann et al. | ................. | 604/1 |
| 5,846,215 A * | 12/1998 | Zygmont | ................. | 604/1 |
| 6,283,933 B1 * | 9/2001 | D'Alessio et al. | ................. | 604/3 |
| 6,358,231 B1 * | 3/2002 | Schindler et al. | ................. | 604/289 |
| 6,375,956 B1 * | 4/2002 | Hermelin et al. | ................. | 424/400 |
| 6,491,940 B1 * | 12/2002 | Levin | ................. | 424/434 |
| 7,582,067 B2 * | 9/2009 | Van Acker | ................. | 604/1 |
| 2002/0133110 A1 * | 9/2002 | Citow | ................. | 604/1 |
| 2005/0171462 A1 * | 8/2005 | Tsaur | ................. | 604/1 |
| 2006/0004035 A1 * | 1/2006 | Barr et al. | ................. | 514/282 |

* cited by examiner

*Primary Examiner* — Melanie Hand
*Assistant Examiner* — Paula Craig
(74) *Attorney, Agent, or Firm* — Schiff Hardin LLP

(57) ABSTRACT

A disposable swab tipped medication applicator containing one or more pharmacologically active agents in an anhydrous crystalline or powdered form at the swab. A method for use of the swab tipped applicator provides for delivery the pharmacological agent(s) to an area of the skin, such as the external auditory canal, preferably after showering or bathing, so that the dry agent is dampened so as to treat conditions of the skin. A package of the prepared applicators is provided in one embodiment, while in another embodiment applicators having two different medicaments are provided in a single package for treatment of a condition.

14 Claims, 1 Drawing Sheet

METHOD FOR TREATMENT OF SKIN DISEASES AND THE LIKE

CROSS-REFERENCE TO RELATED APPLICATION

This application is a divisional application of U.S. patent application Ser. No. 11/080,707, filed Mar. 15, 2005, now U.S. Pat. No. 7,582,067 which is incorporated by reference herein.

BACKGROUND OF THE INVENTION

1. Field of the Invention

The present invention relates generally to method and apparatus for treatment of skin or body tissue and, in particular, to a medicated applicator and a method for treating skin diseases and the like with the applicator.

2. Description of the Related Art

Skin covers the human body and serves as a protection against various diseases and irritants. However, the skin itself is subject to many ailments, diseases and irritations. People seek to treat these diseases and irritations by various treatments, including creams, salves, ointments and powders. Some areas of the skin are more difficult to access with these treatments and so an applicator may be desirable. One such area is the ear canal, or auditory canal. People frequently seek medical attention for skin conditions in the ear canal.

Various kinds of applicators are used on the skin. One such applicator is a small stick on one or both ends of which is provided a fiber swab in the form of a little bud. This swab, which is often of cotton, is used to absorb or remove unwanted fluids or materials from the skin, for example, to remove water or wax from the ear canal. Such swabs can also be used to apply medicaments or cosmetics by dipping the cotton swab into a medicated solution or cosmetic.

Al Ani (U.S. Pat. No. 3,948,265) discloses a medicated applicator having a thin liquid soluble layer of medicament on one or both ends of an elongated carrier formed of a material that is not liquid-absorbing.

Barabino (U.S. Pat. No. 4,740,194) discloses a self-contained liquid swab applicator having a hollow tubing of thin walled plastic for retaining and supplying a liquid. An orifice is formed in the tubing to permit the liquid to exit and a removable tab covers the orifice to secure the orifice until removed. When the orifice is opened, the liquid flows to a swab applicator on the end of the tubing.

Cohen (U.S. Pat. No. 3,976,195) discloses a sealed air-tight package of cotton tipped applicators, with a liquid medicinal material completely absorbed in the swabs.

SUMMARY OF THE INVENTION

The present invention provides, in one embodiment, an applicator having a pharmacologically active substance for applying the substance to the skin or body tissue such as, for example, to the ears and external auditory canal. Another aspect of the invention provides a prepared medication applicator having an elongated holding member with a swab on at least one end wherein the swab has one or more solid pharmacological active agents. In one aspect, the pharmacological active agent is impregnated, mixed or infused into the swab of the applicator. In another aspect, the pharmacological active agent is mixed with a carrier or binder to fix the pharmacological active agent on the swab of the applicator. In yet another aspect, the pharmacological agent is sprayed onto the swab and allowed to dry.

Another embodiment of the invention provides a method of treating the skin by applying an applicator containing one or more dry or substantially dry pharmacological agents to an affected area of the skin, such as the external auditory canal, while the skin is damp. In another embodiment of the method, the applicator containing the dry pharmacological agent is dampened prior to applying it to an affected area of the skin.

DETAILED DESCRIPTION OF THE PREFERRED EMBODIMENTS

Figure 1:
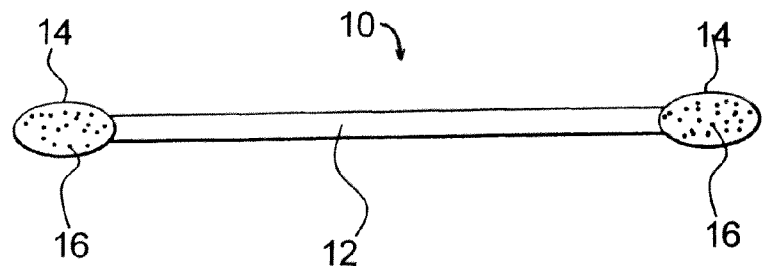
FIG. 1 is a side view of a swab applicator containing one or more pharmacologically active agents according to the present invention.

Referring now to the drawings, there is shown in FIG. 1 a swab applicator 10 having a handle portion 12 which has an absorbent swab 14 on one or both ends. The handle portion 12 is preferably an elongated shaft, tube or rod of a stiff but somewhat flexible material such as plastic, wound paper, wood, or the like. The handle portion 12 may be solid or hollow and have either a smooth or textured external surface. The handle portion of the applicator can be straight, curved, or bent and may be either rigid or flexible, depending on the application.

The swab 14 is of fibers, foam or other pliable absorbent material. In one example, the swab 14 is of cotton fibers wound about the end of the handle portion 12. Other natural or synthetic fibers are of course possible, as is various foam materials. The fibers or foam of the swab may be secured to the handle by an adhesive. The swab 14 may be a separate piece applied to the handle 12 or may be formed on the handle 12 by wrapping, dipping, spraying or otherwise applying the material to the handle.

The shape and size of the applicator 10 varies depending on the area field of application. Applicators which for instance are intended for use in the ear canal include a swab of, for example, 3-7 mm in width at its widest part and of 10-20 mm in length on a handle of between 5 and 10 cm in length. The swab has a tapered shape, generally in the shape of a teardrop. The swab portion can for instance be blunt, spherical, flattened, pointed or any other form suitable for the application purpose. Other shapes and sizes of applicators are of course possible.

One or more pharmacological active agents are provided in or on the swab at one or both ends of the applicator. Preferably, the active agents are anhydrous, but water soluble or dispersible. The active agents of preferred embodiments are in solid form such as crystalline or powders. The active agents may, if necessary, be mixed with other substances such as binders, carriers, adhesives, or the like. The swab may be infused with the pharmacological agent in a liquid form and allowed to dry, or the swab may be impregnated or mixed with the active pharmacological agent in a dry or semi-liquid form. For example, the dry pharmacological agent may be mixed into the fibers of cotton when forming the swab, or may be formed into the foam of a foam swab. A solid inert carrier such as starch, talc, dextrin, microcrystalline cellulose and the like, as described in Smith et al. (U.S. Pat. No. 5,538,732), which is incorporated herein by reference, may be provided for carrying the pharmacological agent. The pharmacological agent may also be put in the form of a liquid by mixing with a suitable solvent. The resulting mixture is either sprayed or otherwise applied to the swab end of the applicator and allowed to dry prior to packaging.

Figure 2:
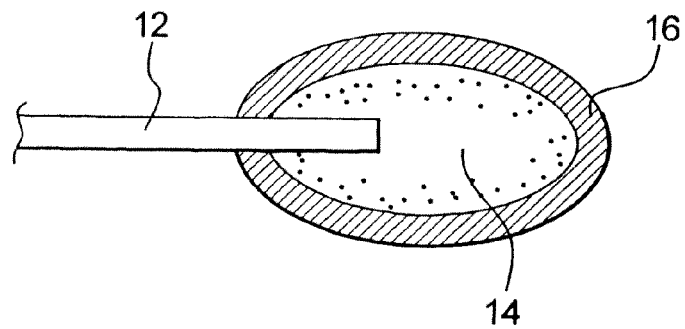
FIG. 2 is an enlarged cross-sectional view of another embodiment of the swab applicator of the present invention.

As shown in FIG. 2, the pharmacological active agent can also be applied as a layer 16 on the swab 14 at the end of the applicator 10. The layer 16 can be on the surface only, diffused somewhat into the swab material, or completely diffused throughout the swab. The pharmacological agent can be mixed homogeneously throughout the swab or can be fixed within or on the swab material on the applicator, so long as they can be dispersed after hydration onto the skin.

In a preferred embodiment, the applicator is a single- or double-ended swab on a semi-flexible handle and the swab includes a dry pharmacological agent for treatment of a skin ailment that may affect the ear canal. The user of the applicator may be afflicted with a skin condition of the external auditory canal and/or ear that causes a dry and/or itchy scaly condition. The user uses the present applicator while the ear canal is damp, such as after showering, bathing or swimming, by inserting the swab portion into the ear canal. The moisture in the ear canal dampens the dry medication, causing it to be applied to the skin within the ear canal. The swab is moved about in and/or around the ear canal, spreading the medication. The applicator is then disposed of.

The dry medication avoids the mess of having the medication applied to, or rubbed off on, unintended areas, such as on other body parts or on bathroom surfaces, clothes or the like. The dry applicator also ensures that debris, hair and other foreign matter do not become adhered to the applicator prior to use. The medication treats, relieves or cures the condition in a simple, cost-effective manner. The medication is applied exactly where needed by the release and/or activation of the medication by the damp ear canal.

Figure 3:
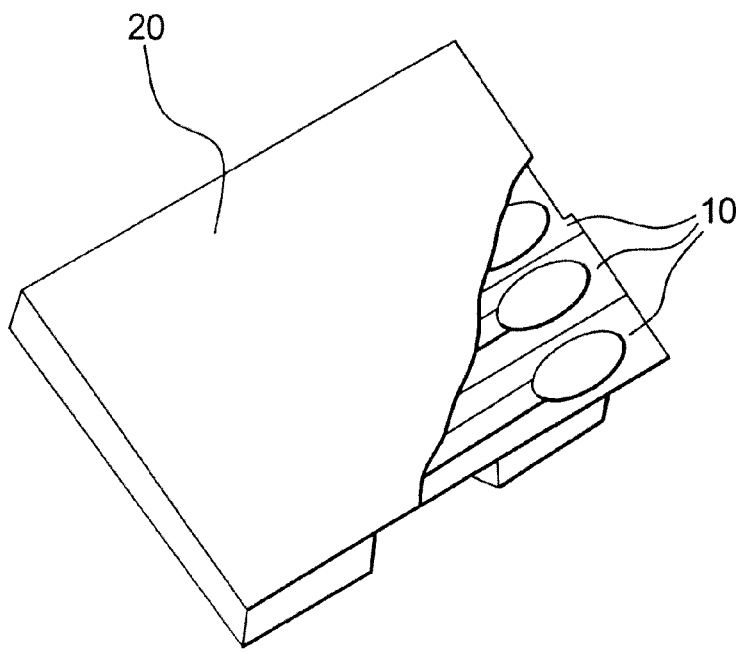
FIG. 3 is a perspective view of a package according to the present invention including a number of swab applicators enclosed by a cover sheet, which has been broken away to show the show the swabs.

In another aspect of the invention, a package 20 of the applicators 10 is provided ready for use, as shown in FIG. 3. The package 20 provides a convenient container for storing the applicators awaiting use, and for retail sale of a number of the applicators.

As shown in FIG. 3, the packaging 20 of the applicators 10 is preferably air-tight to keep the applicators clean and dry and to reduce aging of the active agents to the extent possible. It may also be necessary to protect the applicators from light and any other harmful environmental factors. The packaging preferably has multiple applicators or the applicators may be packed separately as a one-dose disposable package as needed. The packaging is also preferably resealable.

In use, the applicator is pulled out from its package, preferably after showering or bathing, and the end of the applicator on which the active substances already are applied is brought into contact with the moist tissue area or skin area, whereby the rapidly soluble pharmacological active agent is dissolved or activated. If the agent is to be applied onto dry body tissues, it is possible to supply the tissue area or the end of the applicator with one or more drops of a suitable dissolving liquid such as water. After application, the applicator is disposed of.

The applicator of the present invention can be used to deliver pharmacological active agents in a crystalline or powdered form to moist surfaces of the body including but not limited to the oral cavity, external auditory canal and surrounding areas of the ear, nares and adjacent nasal labial folds, alar grooves of the nose, upper and lower eyelids, external medial canthal areas, the oral mucosa, the inframammary areas of the chest, the intertriginous area of the groin, external genitalia, vagina, perianal areas, anus, interdigital spaces, distal subungal areas of finger and toe nail plates, the scalp and any other body surface area that would be moist after showering or bathing.

Although the applicator of the present invention may be used to treat many ailments, preferably, the applicator is used to treat multiple dermatosis of the external auditory canal and ear, such as eczema, psoriasis, neurodermatitis, tinea, seborrheic dermatitis. These are all common dermatosis affecting the ear. Because the external auditory canal and other body surface areas are difficult to reach due to the small size of the orifice, the present applicator containing the appropriate pharmacological agents, preferably in an anhydrous crystalline or powder form, overcomes the difficulty of applying these agents in such tight areas.

Several pharmacological active agents are known to improve or resolve seborrheic dermatitis, eczema and psoriasis, as well as tinea and neurodermatitis, which may be used in the applicator of the present invention. These include generic and trademarked pharmacological active agents including but not limited to antifungals, steroids, retinoids, antipsoriatics, immunomodulators, topical anti-infection agents, topical anti-viral agents, topical anesthetics and antipruitics. Suitable antifungals to treat seborrheic dermatitis and tinea include Ketoconazole, Ciclopiroxolamine, Terbinafine, Clotrimazole, Miconazole Nitrate, Butenafine HCl, Nystatin, Naftifine HCl, Oxiconazole, Selenium Sulfide, Econazole Nitrate, Tolnaftate, Sulconazole Nitrate and Sertaconazole Nitrate. Suitable steroids for the treatment of seborrheic dermatitis, eczema, neurodermatitis and psoriasis include Hydrocortisone, Aclometasone, Dipropionate, Triamcinolone Acetonide, Flurandrenolide, Fluticasone Propionate, Desoximetasone, and Halobetasol Propionate. Suitable antipsoriatics such as the Vitamin D derivative Calcipotriene and retinoids such as Tazarotene and Tretinoin may be used for treating psoriasis. Suitable immunomodulators for the treatment of seborrheic dermatitis, eczema and psoriasis include Pimecrolimus and Tacrolimus. Suitable topical anti-infectant agents include Mupirocin, Neosporin, Bacitracin Silver Sulfadiazine, Chloramphenicol, Aminoclycosides, Gentamicin, Sodium Sulfacetamide, Neomycin Sulfate, Neomycin, Bacitracin, Polymyxin B Sulfate, Nitrofurazone, Chlorhexidine Gluconate. Suitable topical anesthetics include Lidocaine, Prilocaine and Tetracaine and antipruitics such as Doxepin HCL for pruritis and neurodermatitis.

In a further embodiment of the invention, applicators are provided with different medicaments that can be used to treat a single or multiple ailments. The applicators with different medicaments can be provided in different packages or together in a single package. It is preferred that the applicators having the different medicaments include indicators to differentiate between the different medicaments. The indicators can be the trade name or generic name of the medicament, can be symbols or other indicators or can be indicated by colors.

The present applicator provides a convenient means for applying treatments to pre-cancerous conditions of the skin, to skin cancer, and to warts and the like. An immune modulator such as Aldara, a preparation of imiquimod, is preferred for such applications. Other immunomodulators are included within the scope of this invention as well. This provides a handy way to provide regular application of a treatment to pre-cancerous sites on the skin.

In a particular embodiment, a package of applicators is provided with two different medicaments for treatment of a single ailment. The applicators having the different medicaments are indicated with different colors to indicate the medicament and to provide a visual clue to the time of day to use the applicator. For example, for treatment of fungal infections of the ear canal, yellow colored applicator having a steroid for use in the morning and a blue or dark blue applicator having an antifungal agent for use in the evening or just before going to bed. The colors of the applicators provide visual clues to the user as to when to use each medicament. It is foreseeable to provide a two-ended applicator with one medicament on each end, but it is preferred to provide separate applicators for each medicament so that a used applicator does not have to be saved for later use. The packaging of these applicators may include reminders or indicators as to the use of each different applicator as well.

The present invention has the advantage of providing an applicator that is safe, convenient and very effective at delivering pharmacological active agents onto the skin and tissues inside the moist orifices of the body. The stability of the pharmacologically active ingredients is increased by keeping them sterile and dry. Pharmacologically active ingredients maintain their properties much longer when in a dry and sterile state as compared to when in liquid form. The applicators are further protected from light, humidity and bacteria in air-tight packages.

The applicators are advantageous to use in homes, hospitals and at doctor's offices because the applicators can be packed under sterile conditions in a single dose discardable packing, which will eliminate the risk of contamination. The inventive applicators are also economical for use at home, as the waste percentage is much lower and the life span of the applicators is much longer. Each applicator has an amount of active substance needed for one dose of the medication, which is generally going to be less than the corresponding amount applied in solution in an ear-drops bottle, for example, and thus prevents wastage. The applicators are also much easier for home use compared to liquid drops, that may run out of the ear or even never reach the afflicted area due to the difficulty in attempting self medication of the ear canal.

The applicators are convenient to carry, as in the pocket or purse, easily accessible, sanitary and provide a fresh medicament for each use. The applicators are handy and can be used swiftly which means time is saved, which is especially appreciated by a busy doctor, hospital personnel and the individual consumer.

Although other modifications and changes may be suggested by those skilled in the art, it is the intention of the inventors to embody within the patent warranted hereon all changes and modifications as reasonably and properly come within the scope of their contribution to the art.

I claim:

1. A method of treatment of dermatosis of an external auditory canal and ear of a patient, comprising the steps of:
    showering or bathing the patient so as to dampen the external auditory canal and ear;
    selecting a first swab having a first pharmacological active agent from a package of medicated swabs where the first swab is selected based on a first time of day indicia on the first swab, said package of medicated swabs including second swabs having a second pharmacological active agent and being distinguished from the first swab by a second time of day indicia, said second pharmacological active agent hem a different pharmacological active agent than said first pharmacological active agent;
    removing the first swab from the package of medicated swabs;
    applying the first swab in a dry condition to dampened surfaces of the external auditory canal and car so as to dampen a dry pharmacological active agent on the first swab;
    applying the first pharmacological active agent to the patient's ear using the dampened first swab;
    selecting a second swab having a second pharmacological active agent from the package where the second swab is selected based on the second time of day indicia;
    removing the second swab from the package of medicated swabs;
    applying the second swab in a dry condition to dampened surfaces of the external auditory canal and ear so as to dampen dry pharmacological active agent on the second swab; and
    applying the second pharmacological active agent to the patient's ear using the dampened second swab.

2. A method as claimed in claim 1, wherein at least one of said first and second pharmacological active agents is in a powder form.

3. A method as claimed in claim 1, wherein at least one of said first and second pharmacological active agents is in a crystalline form.

4. A method as claimed in claim 1, wherein at least one of said first and second pharmacological active agents is mixed into fibers of said swab.

5. A method as claimed in claim 1, wherein at least one of said first and second pharmacological active agents is impregnated into said swab.

6. A method as claimed in claim 1, wherein at least one of said first and second pharmacological active agents is infused into said swab.

7. A method as claimed in claim 1, wherein at least one of said first and second pharmacological active agents has been applied to said swab in wet form and allowed to dry.

8. A method as claimed in claim 1, further comprising: an inert material selected from the group consisting of binders and adhesives in said swab.

9. A method as claimed in claim 1, further comprising the step of: resealing the package following at least one of said steps of removing the first swab or removing the second swab, wherein said package is a resealable airtight container.

10. A method as claimed in claim 1, wherein said first and second pharmacological active agents are selected from the group consisting of anti-fungal agents, steroids, retinoids, antipsoriatics, immunomodulators, topical anti-infection agents, topical anti-viral agents, topical anesthetics and anti-pruitics.

11. A method as claimed in claim 1, wherein at least one said pharmacological active agent is selected from the group consisting of Ketoconazole, Ciclopiroxolamine, Terbinafine, Clotrimazole, Miconazole Nitrate and steroids.

12. A method as claimed in claim further comprising the step of: dampening at least one of said first and second swabs by immersing a portion of the swab in a liquid prior to said step of applying the corresponding pharmacological active agent.

13. A method as claimed in claim 1, wherein said time of day indicators include mutually different colors of said first and second swabs.

14. A method as claimed in claim 1, wherein said first pharmacological active agent is a steroid and said second pharmacological active agent is an antifungal agent.

* * * * *